United States Patent [19]

Bogert et al.

[11] Patent Number: 4,896,661
[45] Date of Patent: Jan. 30, 1990

[54] MULTI PURPOSE ORTHOPEDIC RATCHETING FORCEPS

[75] Inventors: Roy Bogert, Lincoln Park, N.J.; Michael W. Chapman, Sacramento, Calif.; Charles C. Edwards, Baltimore, Md.; Dana C. Mears, Pittsburgh, Pa.

[73] Assignee: Pfizer, Inc., New York, N.Y.

[21] Appl. No.: 152,455

[22] Filed: Feb. 5, 1988

[51] Int. Cl.⁴ ................... A61B 17/18; A61B 17/28
[52] U.S. Cl. ............................ 606/86; 128/17; 81/337; 81/328; 81/423; 81/427.5; 606/207; 606/208
[58] Field of Search .......... 128/346, 321, 322, 92 VZ, 128/345, 17, 18, 303 R; 604/106; 433/159; 81/318, 319, 325, 328, 423, 427.5, 337, 338

[56] References Cited
U.S. PATENT DOCUMENTS

| 2,427,128 | 9/1947 | Ettinger | 128/92 VZ |
| 2,669,992 | 2/1954 | Curutchet | 128/321 |
| 3,470,872 | 10/1969 | Grieshaber | 128/321 X |

FOREIGN PATENT DOCUMENTS 401732  9/1909  France .................. 128/321

Primary Examiner—Michael H. Thaler
Attorney, Agent, or Firm—Walter G. Maple, Jr.; Nicholas L. Coch; John E. Kidd

[57] ABSTRACT

A forceps for use in orthopedic surgical procedures having readily interchangeable tip elements and a reversible ratchet mechanism, for controlling the tip elements. A variety of tips for compression and distraction are provided. The ratchet mechanism permits controlled increments of force to be applied to the tips.

3 Claims, 4 Drawing Sheets

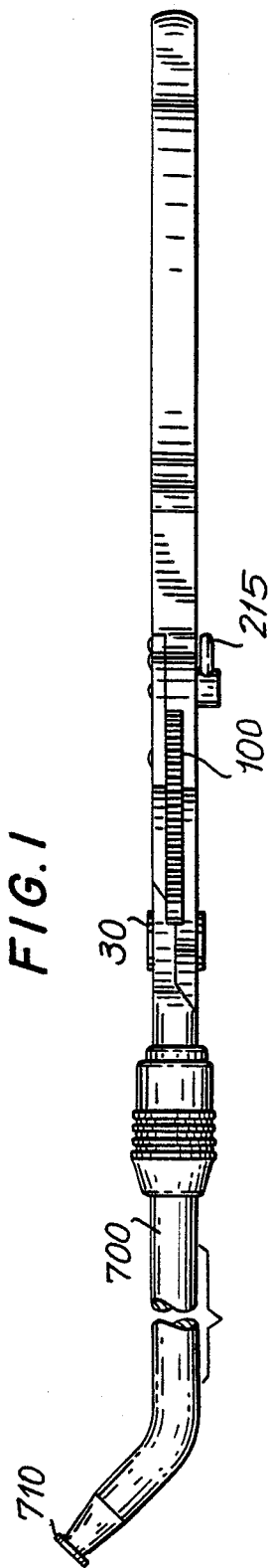
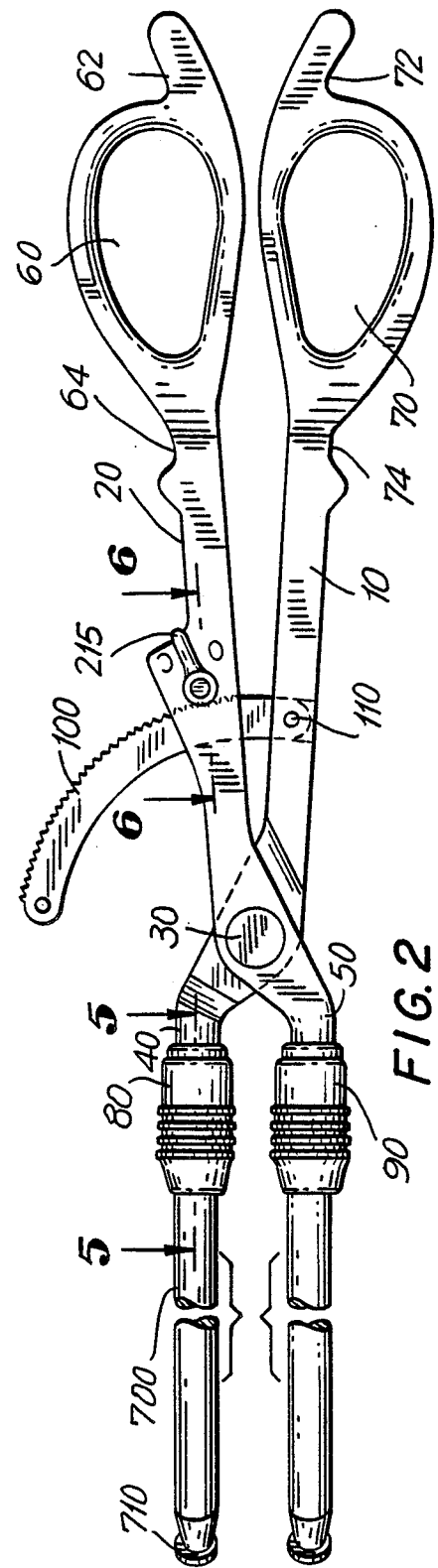

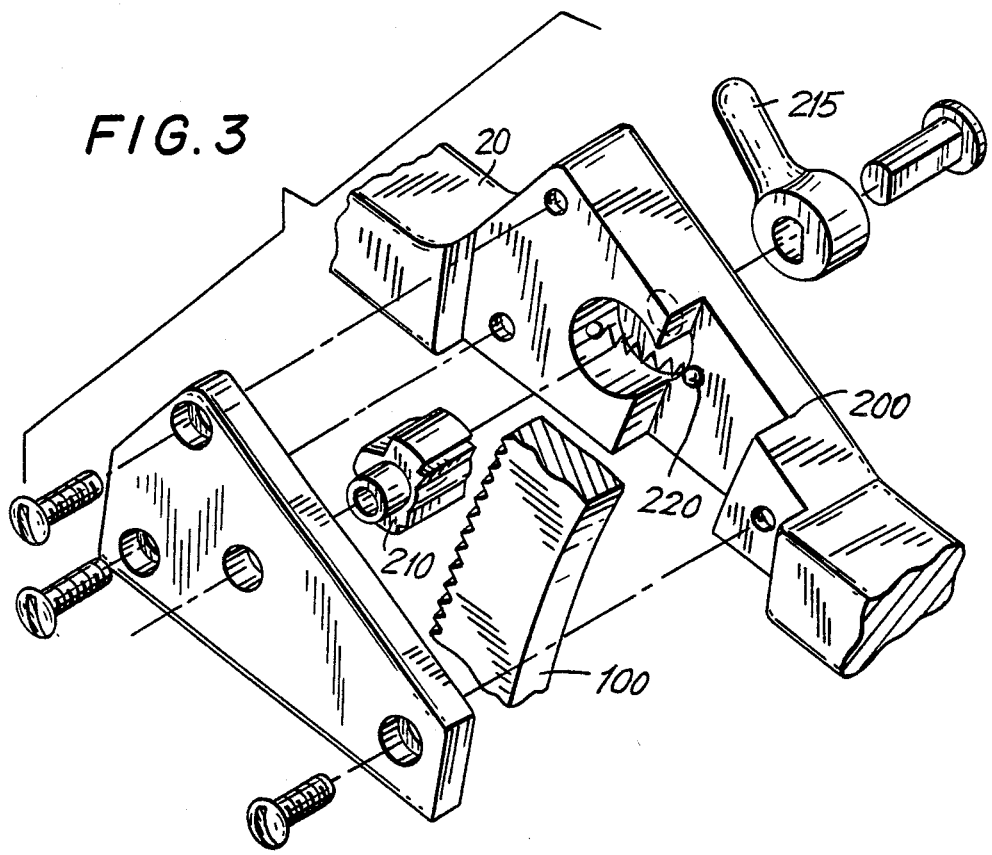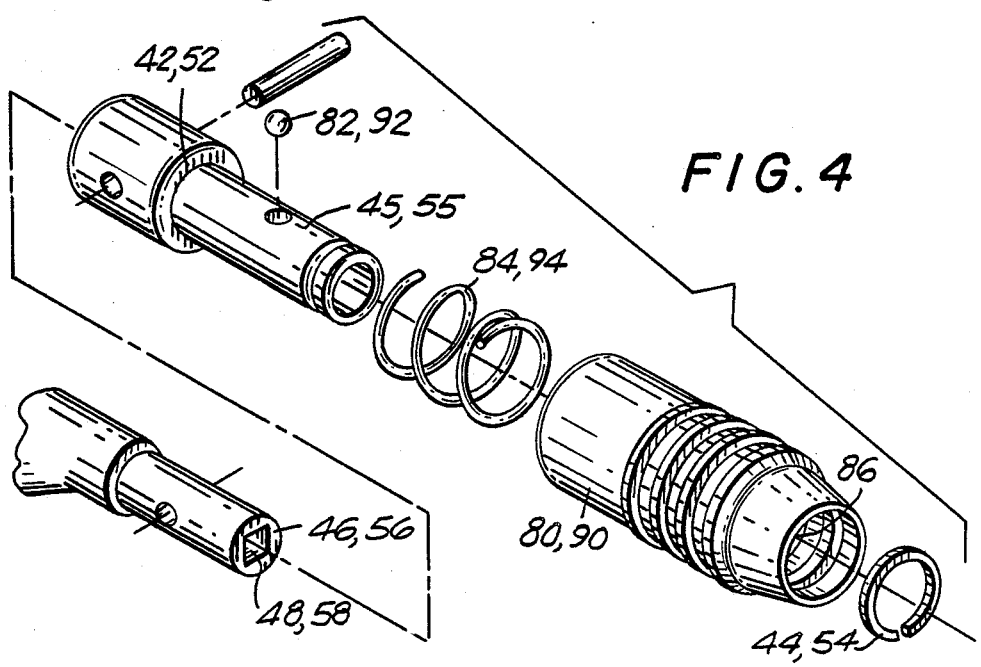

MULTI PURPOSE ORTHOPEDIC RATCHETING FORCEPS

BACKGROUND OF THE INVENTION

1. Field of the Invention

This invention relates broadly to clamping devices used in orthopedic surgery and more specifically to forceps used to manipulate and hold the bone for fixation of fractures.

2. Description of the Related Art

A number of efforts have been made in the art to provide bone-clamping and manipulating devices for use during orthopedic surgery. An exemplary clamping device using a hemostat clamp design is shown in U.S. Pat. No. 4,475,544 to Reis. It has also been known to adapt locking jaw pliers to the temporary clamping of a fractured bone under repair. A ratcheting arrangement for temporary clamping is shown in U.S. Pat. No. 4,009,712 to Burstein, et al.

None of these prior art devices are entirely satisfactory for the wide range of manipulative procedures typically required in employing an internal screw and plate fixation system for the treatment of bone fractures. In addition, more that one such device is required to provide clamping, compression and distraction. It is an object of the present invention to provide all of these functions by utilizing easily changed tip portions on a forceps device having a reversible ratchet mechanism.

SUMMARY OF THE INVENTION

The present invention is a forceps having interchangeable tip elements and a reversible ratchet mechanism for controlling such tip elements. Such a forceps is particularly useful in orthopedic procedures because a variety of tip elements can be used for compression and distraction of plate and screw fixation systems as well as gripping and manipulating the bone. The reversible ratchet mechanism permits controlled increments of force in either opening or closing the forceps jaws. In addition, the hand grip of the forceps of the invention has been shaped for comfort and ease of use.

The forceps of the invention are particularly useful as a part of a modular system of internal fixation of bone fractures. Such a system utilizes a minimum number of plates that are employed interactively as to permit compressive, distractive and turning manipulation of the bone parts. The forceps of the invention make such manipulations possible by permitting use of a wide range easily of interchangeable tip configurations and providing incremental ratchet adjustment of either compressive or distractive forces.

These and other advantages of the invention may best be understood by reference to the following detailed description and accompanying drawings.

BRIEF DESCRIPTION OF THE DRAWINGS

FIG. 1 is a side view of the forceps of the invention showing an interchangeable tip element secured in the jaw portion.

FIG. 2 is to view of the forceps of the invention showing the shape of the hand grip portions and the ratchet control lever.

FIG. 3 is an exploded view of the ratchet control mechanism of the forceps of the invention.

FIG. 4 is an exploded view of the interchangeable tip securing mechanism of the forceps of the invention.

DETAILED DESCRIPTION OF THE INVENTION

Figure 5:
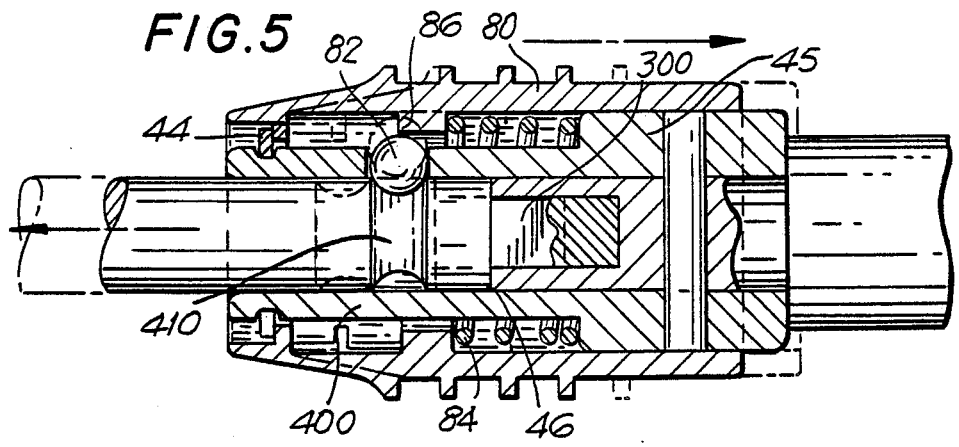
FIG. 5 is an illustration of the operation of interchangeable tip securing mechanism of the forceps of the invention.

Referring to FIG. 1, there is shown a side view of a forceps device in accordance with the invention. As can be seen in FIG. 2, the device is formed by joining elongated arms 10, 20 by pivot pin 30 thereby forming opposing coplanar jaw portions 40, 50 at one end of arms 10, 20.

Each arm 10, 20 has at its other end an ovoid opening 60, 70 which, in conjunction with finger rests 62, 64, 72 and 74, form a hand grip for the forceps device.

The jaw portions 40, 50 have a mechanism for securing removable tip portions. This mechanism consists of respective sleeves 80, 90. As can be seen in FIG. 4, each of sleeves 80, 90 are spring loaded by springs 84, 94 between stops 42, 52 and retainer rings 44, 54 on hollow cylindrical extensions 45, 55 of jaw portions 40, 50 respectively. Detent balls 82, 92 are held in respective detent holes by sleeves 80, 90. In operation, a tip such as shown in FIG. 5 is removably secured by this mechanism by inserting the grooved end portion of the tip into hollow cylindrical extension 45 for example. For ease of understanding physically identical portions of the tips shown in FIGS. 1, 5, 10, 11 and 12 bear the same numerical designation. When the leading shoulder 400 of the tip is stopped by detent ball 82, sleeve 80 is manually urged against spring 84 bringing groove 86 into alignment with detent ball 82 which moves outwardly into groove 86 permitting the leading shoulder 400 of the tip to move, to stop 46. When the tip is thus seated, groove 410 of the tip is aligned with detent ball 82 and release of sleeve 80 which is urged toward retaining ring 44 by spring 84, locks detent ball 82 into groove 410 of the tip.

Figure 6:
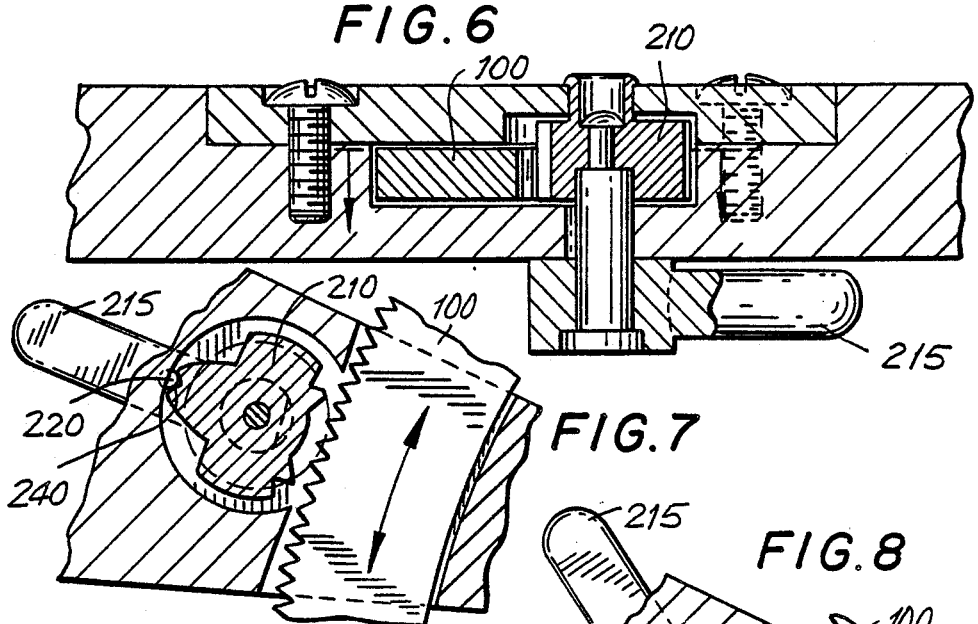
FIG. 6 is a side cut away view of the ratchet mechanism of the forceps of the invention.
Figure 7:
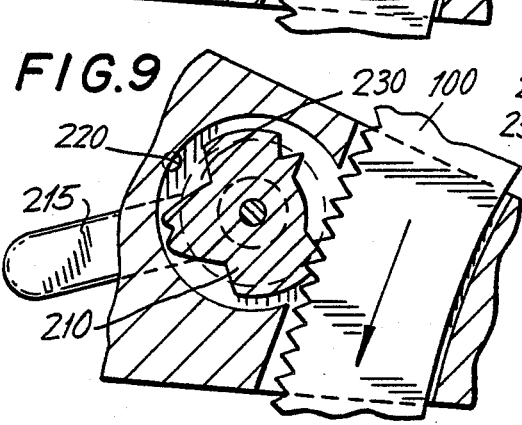
FIG. 7 is an illustration of the ratchet mechanism in the disengaged position.
Figure 8:
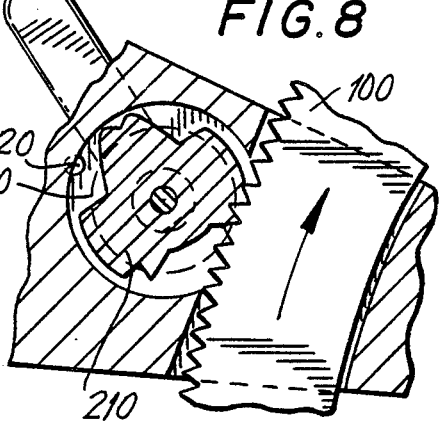
FIG. 8 is an illustration of the ratchet mechanism engaged to permit only ratchet controlled closing of the jaws of the forceps of the invention.
Figure 9:
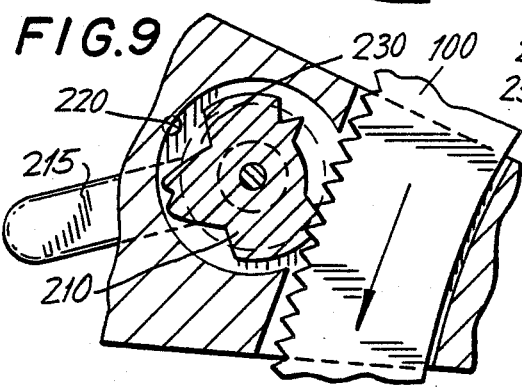
FIG. 9 is an illustration of the ratchet mechanism engaged to permit only ratchet controlled opening of the jaws of the forceps of the invention.

Referring now to FIGS. 2, 3 and 6 there is shown the ratchet mechanism of the forceps of the invention. A curved ratchet toothed member 100 is secured in a suitable channel of arm 10 by pin 110. Member 100 extends inwardly from arm 10 towards arm 20 and passes through pawl mechanism chamber 200 of arm 20. A pawl 210, controlled by pawl lever 215, is urged towards the teeth of member 100 by spring loaded ball 220. As shown in FIGS. 7, 8 and 9 there are three detents 230, 240, 250 in pawl 210 engageable by ball 220. Pawl lever 215 is used to position pawl 210 at one of the three detents; FIG. 9 shows detent 230 engaged by ball 220 to permit ratcheting open jaws 40, 50; FIG. 7 shows detente 240 engaged by ball 220 to disengage pawl 210 permitting jaws 40, 50 to open or close without ratcheting; and FIG. 8 shows detent 250 engaged by ball 220 to permit ratcheting closed jaws 40, 50.

As was stated previously, the forceps of the invention are particularly useful in bone and joint surgical procedures therefore, a number of interchangeable tips for this purpose are shown in FIGS. 1, 10, 11 and 12.

In many typical orthopedic procedures, some form of fracture fixation is used. The forceps of the invention are uniquely adapted to use with fixation systems utilizing plates screwed to the fractured bone and intended to span and compress the fracture.

Figure 10:
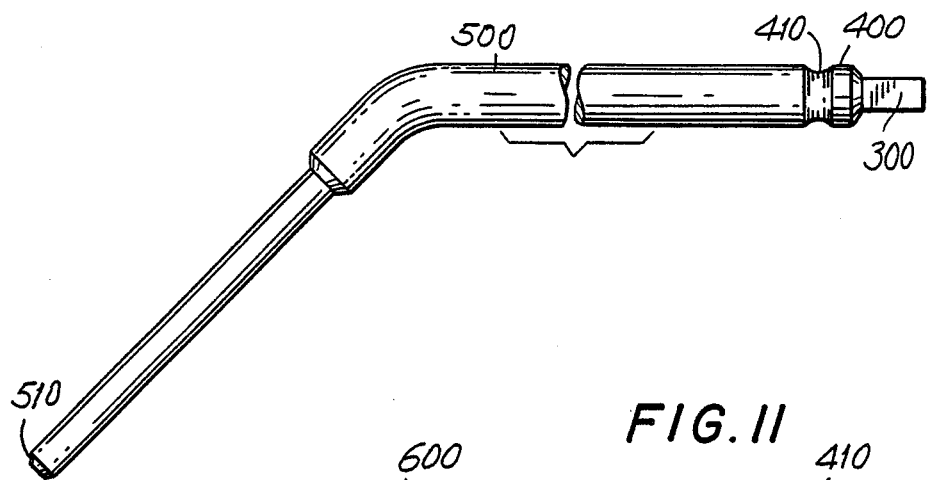
FIG. 10 is a fixed position interchangeable tip element for use with the forceps of the invention.

The tip shown in FIG. 10 is a fixed tip 500 used in the forceps of the invention compression and distraction in a plate and screw fixation system. This tip is a fixed position tip; in that square stud 300 fits into recesses 48, 58 of jaw portions 40, 50 and is thereby prevented from rotating about its axis. When tips of this type are secured to the jaw portion of the forceps of the invention, movable plates spanning a fracture can be adjusted by inserting tip ends 510 into holes in the plates and then ratcheting the jaws closed for a controlled compression or ratcheting the jaws open for distraction. Once the desired position and compression are achieved, the forceps will stay locked in position until the plates are permanently fixed.

Figure 11:
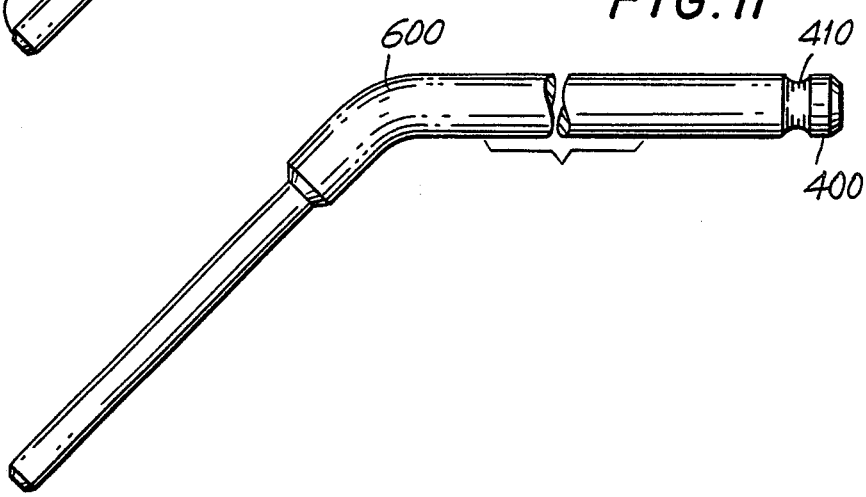
FIG. 11 is a swiveling interchangeable tip element for use with the forceps of the invention.

Referring now to FIG. 11 there is shown a tip 600 identical to the 500 except that it does not have locking stud 300 and can therefore rotate about an axis through groove 410. A tip of this type in one jaw of the forceps of the invention utilized with a fixed tip 500 in the other jaw permits axial rotation of the bone during manipulation prior to fixation.

Referring now to FIG. 1 there is shown another tip 700 with a specialized end piece 710 for use with plate fixation systems specifically designed with holes for accommodating such tip ends.

Figure 12:
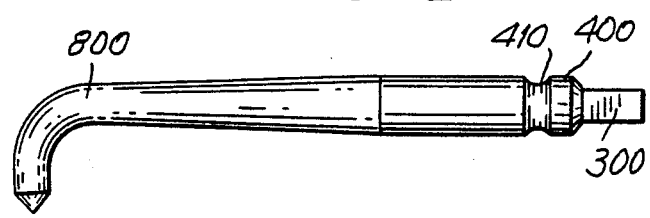
FIG. 12 is an interchangeable tenaculum tip element for use with the forceps of the invention.

Finally referring to FIG. 12 there is shown a tenaculum tip 800 for use with the forceps of the invention. Two such tips secured in the jaw portion such that the points 810 are in opposition are used to grip and manipulate bones with the forceps of the invention.

The foregoing description of a preferred embodiment of the forceps of the invention is not intended to limit the scope of the invention which is described in the appended claims.

We claim:
1. A forceps device comprising:
 (a) a first elongate arm having a hand grip portion at a proximal end;
 (b) a second elongate arm having a hand grip portion at a proximal end;
 (c) said first and second arms being joined at a pivot point to form opposing co-planar jaw portions at their distal ends;
 (d) said jaw portions being adapted to removably secure interchangeable tip portions;
 (e) said first arm having a ratchet toothed member secured thereto intermediate said pivot point and said hand grip portion;
 (f) said second arm having a multiposition pawl mechanism positioned to engage said ratchet toothed member such that in one position of said pawl, said arms pivot to ratchet open said jaw portions, in a second position of said pawl, said arms pivot to ratchet closed said jaw portions and in a third position, said pawl is disengaged from said ratchet toothed member, whereby suitable tip portions are ratcheted to compress or distract a work piece.

2. The forceps device of claim 1 wherein said hand grip portions are shaped to form rounded ovoid openings with the widest portion at the proximal end and further comprise curved finger rest portions at both the distal and proximal ends of said openings.

3. The forceps device of claim 1 wherein said jaw portions removably secure said tip portions by way of a spring loaded sleeve, ball detent and groove mechanism.

* * * * *